(12) United States Patent
Xu et al.

(10) Patent No.: US 11,484,373 B2
(45) Date of Patent: Nov. 1, 2022

(54) FLEXIBLE SURGICAL INSTRUMENT SYSTEM

(71) Applicant: Beijing Surgerii Technology Co., Ltd., Beijing (CN)

(72) Inventors: Kai Xu, Beijing (CN); Tianlai Dong, Beijing (CN); Zhengchen Dai, Beijing (CN); Shu'an Zhang, Beijing (CN); Jiangran Zhao, Beijing (CN); Huan Liu, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 918 days.

(21) Appl. No.: 16/288,184

(22) Filed: Feb. 28, 2019

(65) Prior Publication Data
US 2019/0254648 A1 Aug. 22, 2019

Related U.S. Application Data

(63) Continuation of application No. PCT/CN2017/099757, filed on Aug. 30, 2017.

(30) Foreign Application Priority Data

Aug. 31, 2016 (CN) .......................... 201610796073.5

(51) Int. Cl.
*A61F 2/95* (2013.01)
*A61B 34/30* (2016.01)
(Continued)

(52) U.S. Cl.
CPC ........ *A61B 34/30* (2016.02); *A61B 17/00234* (2013.01); *A61B 17/29* (2013.01);
(Continued)

(58) Field of Classification Search
CPC ............ A61B 17/29; A61B 17/320068; A61B 2017/00314; A61B 2017/00323; A61B 2017/00398
See application file for complete search history.

(56) References Cited

U.S. PATENT DOCUMENTS

| 2006/0178556 A1 | 8/2006 | Hasser et al. |
| 2006/0191623 A1* | 8/2006 | Lutz .......................... C09J 4/06 156/293 |

(Continued)

FOREIGN PATENT DOCUMENTS

| CN | 102512216 A | 6/2012 |
| CN | 103315781 A | 9/2013 |

(Continued)

OTHER PUBLICATIONS

Search Report in corresponding Japanese Application No. 2019-531520 dated May 18, 2021 (20 pages including English machine translation).
(Continued)

*Primary Examiner* — Muhammad S Islam
(74) *Attorney, Agent, or Firm* — Bayes PLLC

(57) ABSTRACT

Disclosed is a flexible surgical instrument system comprising a flexible surgical instrument and a driving unit. The flexible surgical instrument can comprise a flexible continuous body structure composed of a distal structural body, a proximal structural body and a middle connecting body. The distal structural body can comprise a distal segment, comprising a distal spacing disk, a distal fixation disk and structural backbones. The proximal structural body can comprise a proximal segment comprising a proximal spacing disk, a proximal fixation disk and structural backbones. The middle connecting body can comprise channel fixing plates and a structural backbone guide channel. The driving unit can comprise a driving unit fixing plate. Linear motion
(Continued)

mechanisms are provided between the driving unit fixing plate and the channel fixing plate near the proximal structural body, an output end of each of the linear motion mechanisms is securely connected to a first driving backbone.

20 Claims, 10 Drawing Sheets

(51) Int. Cl.
*A61B 17/00* (2006.01)
*A61B 17/29* (2006.01)
*A61B 17/32* (2006.01)

(52) U.S. Cl.
CPC ............. *A61B 17/320068* (2013.01); *A61B 2017/00314* (2013.01); *A61B 2017/00323* (2013.01); *A61B 2017/00398* (2013.01); *A61B 2034/301* (2016.02)

(56) References Cited

U.S. PATENT DOCUMENTS

| | | |
|---|---|---|
| 2011/0028991 A1 | 2/2011 | Ikeda et al. |
| 2015/0265355 A1 | 9/2015 | Prestel et al. |
| 2018/0098849 A1* | 4/2018 | Yellin ................ A61B 17/3468 |

FOREIGN PATENT DOCUMENTS

| | | |
|---|---|---|
| CN | 103948435 A | 9/2013 |
| CN | 103340707 A | 10/2013 |
| CN | 103340731 A | 10/2013 |
| CN | 103707322 A | 4/2014 |
| CN | 104490477 A | 4/2015 |
| CN | 104758060 A | 7/2015 |
| CN | 105690378 A | 6/2016 |
| CN | 105751210 A | 7/2016 |
| CN | 106175850 A | 12/2016 |
| CN | 106308936 A | 1/2017 |
| EP | 1274480 B1 | 7/2006 |
| EP | 2008594 A2 | 12/2008 |
| JP | 2007175502 A | 7/2007 |
| KR | 20120003091 A | 1/2012 |
| WO | 2009094670 A1 | 7/2009 |

OTHER PUBLICATIONS

International Search Report of PCT/CN2017/099757.
The first Office Action of CN application 2016107960735.
The search report of EP application 178454633.
Xu Kai et al: "Design of a hyper-redundant continuum manipulator for intra-cavity tasks", 2014 IEEE International Conference on Robotics and Biomimetics (ROBIO 2014), IEEE, Dec. 5, 2014.

* cited by examiner

FLEXIBLE SURGICAL INSTRUMENT SYSTEM

CROSS-REFERENCE TO RELATED APPLICATIONS

This patent application is a continuation of International Application No. PCT/CN20 17/099757, filed one Aug. 30, 2017, which claims the priority of Chinese patent application No. 201610796073.5 filed on Aug. 31, 2016, entitled "Flexible surgical instrument system comprising driving backbone", which is incorporated herein by reference in its entirety.

TECHNICAL FIELD

The present invention relates to a flexible surgical instrument system comprising a driving backbone, belonging to the field of medical instruments.

BACKGROUND

Multi-port laparoscopic minimally invasive surgery has occupied an important position in surgery because of its small wound and rapid postoperative recovery. The existing da Vinci surgical robot of the Intuitive Surgical, Inc. assists doctors to complete the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been developed and have less trauma to the patient and higher postoperative outcomes. However, in the single-port laparoscopic surgery and the natural orifice transluminal non-invasive surgery, all surgical instruments including a visual illumination module and a surgical operating arm have access to the surgical site through a single channel, which is extremely stringent for the preparation of the surgical instruments. The distal structure of the existing surgical instrument mainly consists of multiple rods hinged in series, and is driven by a pulling force from a wire rope, so that the surgical instrument can be turned at a hinge joint. Since the wire rope has to be continuously tensioned by a pulley, this driving method is difficult to further miniaturize the surgical instrument, and is also difficult to further improve the moving performance of the instrument.

Although the Intuitive Surgical, Inc. recently introduced a da Vinci Single-Site (SS-type da Vinci) surgical robot, in which the original rigid surgical instrument is modified into a semi-rigid surgical instrument and a pre-bent sleeve is additionally provided so as to improve the moving performance of the surgical instrument to a certain extent, it is impossible to fundamentally solve the problems faced by the traditional surgical instruments.

SUMMARY

In view of the above problems, an object of the present invention is to provide a flexible surgical instrument system comprising a driving backbone, which flexible surgical instrument system can be better applied to a surgical robot system that passes through a natural orifice of the human body or a single surgical incision and performs an operation.

In order to achieve the above-mentioned object, the following technical solution is used for the present invention: a flexible surgical instrument system, comprising a flexible surgical instrument and a driving unit, wherein the flexible surgical instrument comprises a flexible continuous body structure composed of a distal structural body, a proximal structural body and a middle connecting body; the distal structural body comprises at least one distal segment comprising a distal spacing disk, a distal fixation disk and structural backbones; the proximal structural body comprises a proximal segment comprising a proximal spacing disk, a proximal fixation disk and structural backbones; the middle connecting body comprises channel fixing plates and a structural backbone guide channel provided between the channel fixing plates; the structural backbones of the distal segment are securely connected in one-to-one correspondence to or are the same as the structural backbones of the proximal segment, one end of each of the structural backbones is securely connected to the proximal fixation disk, and the other end of the structural backbones passes through the proximal spacing disk, the structural backbone guide channel, and the distal spacing disk in sequence, and is securely connected to the distal fixation disk; and the driving unit comprises a driving unit fixing plate, a plurality of linear motion mechanisms for converting a rotational motion input into a linear motion output are provided between the driving unit fixing plate and the channel fixing plate near the distal structural body, an output end of each of the linear motion mechanisms is securely connected to a first driving backbone, one end of the first driving backbone is securely connected to one end of a second driving backbone via an adapter unit, and both the other end of the first driving backbone and the other end of the second driving backbone pass through the proximal spacing disk and are then securely connected to the proximal fixation disk.

Preferably, the number of the proximal segments is equal to the number of the distal segments.

In one embodiment, the linear motion mechanism may comprise a first lead screw, a first sliding block and a first shaft, the first lead screw is rotatably supported between the two channel fixing plates, a rear end of the first lead screw passes through the channel fixing plate near the proximal structural body side and extends rearward, the first shaft is fixedly connected between the two channel fixing plates, and the first sliding block is slidably connected to the first shaft and is threadly connected to the first lead screw; and the first driving backbone is securely connected to the first sliding block.

In one embodiment, the adapter unit may comprise a routing backbone, structural backbone connectors, and a routing backbone guide channel, two ends of the routing backbone guide channel are securely connected to a front side of the channel fixing plate near the distal structural body, the routing backbone passes through the routing backbone guide channel, and each of two ends of the routing backbone is securely connected to one of the structural backbone connectors, wherein one of the structural backbone connectors is securely connected to one end of the first driving backbone, and another structural backbone connector is securely connected to one end of the second driving backbone.

In one embodiment, the routing backbone may be composed of a plurality of elastic structural backbones which are symmetrically distributed with the first driving backbone or the second driving backbone taken as the center.

In one embodiment, a driven gear is securely connected to the first lead screw located on a front side of the driving unit fixing plate, the driven gear is engaged with a driving gear rotatably supported on the driving unit fixing plate, and a gear shaft of the driving gear passes through the driving unit fixing plate and is securely connected to a male coupling.

In one embodiment, a surgical end effector may be provided at a front end of the distal structural body, and a surgical end effector actuation wire connected at one end to the surgical end effector passes through the distal structural body, the surgical end effector actuation wire is connected at the other end to a surgical end effector driving mechanism; the surgical end effector driving mechanism comprises a surgical end effector driving mechanism fixing plate provided between the two channel fixing plates, a second lead screw is provided between the surgical end effector driving mechanism fixing plate and the driving unit fixing plate, a front end of the second lead screw passes through the channel fixing plate near the proximal structural body side, a second sliding block is connected, by a threaded fit, to the second lead screw between the channel fixing plate and the surgical end effector driving mechanism fixing plate, the second sliding block is slidably provided on a second shaft, and the second shaft is fixedly connected between the channel fixing plate and the surgical end effector driving mechanism fixing plate; a actuation wire guide channel is securely connected between the surgical end effector driving mechanism fixing plate and the channel fixing plate near the distal structural body side, and a rear end of the surgical end effector actuation wire passes through the actuation wire guide channel and is then securely connected to the second sliding block; and the driving unit further comprises a multi-motor assembly which comprising a motor fixing plate and a first motor securely connected to the motor fixing plate, an output shaft of the first motor being directly or indirectly connected to the second lead screw, to transfer a rotational motion of the output shaft of the first motor to the second lead screw and convert the rotational motion into a linear motion output of the second sliding block.

In one embodiment, the flexible surgical instrument system may further comprise a flexible surgical instrument housing, wherein the driving unit fixing plate and the channel fixing plates are both securely connected to the flexible surgical instrument housing, and the proximal structural body and the middle connecting body are both located inside the flexible surgical instrument housing; a rear end of the flexible surgical instrument housing is connected to the multi-motor assembly via a sterile barrier which comprising a sterile barrier support plate, a sterile barrier cover securely connected to an outer periphery of the sterile barrier support plate, and a plurality of female couplings rotatably connected to the sterile barrier support plate; the multi-motor assembly comprises a motor fixing plate and a second motor securely connected to the motor fixing plate, the motor fixing plate being connected to the sterile barrier support plate via a connecting pin base; and a front end of the female coupling is connected to the male coupling, and another end of the female coupling is securely connected to an output shaft of the second motor via another male coupling.

In one embodiment, the flexible surgical instrument system may further comprise a flexible surgical instrument housing, a sterile barrier and a multi-motor assembly, wherein the driving unit fixing plate and the channel fixing plates are both securely connected to the flexible surgical instrument housing, and the proximal structural body and the middle connecting body are both located inside the flexible surgical instrument housing; the multi-motor assembly comprises a motor fixing plate and a third motor securely connected to the motor fixing plate, the flexible surgical instrument housing being connected to the motor fixing plate via the sterile barrier; the multi-motor assembly further comprises a multi-motor assembly housing, the motor fixing plate being rotatably connected to the multi-motor assembly housing, and an internal ring gear being securely connected to an internal wall of the multi-motor assembly housing; and an output shaft of the third motor is securely connected to an integral rotary input gear which is engaged with the internal ring gear.

In one embodiment, the flexible surgical instrument system may further comprise a flexible surgical instrument housing, a sterile barrier, a multi-motor assembly, and a linear module, wherein the driving unit fixing plate and the channel fixing plates are both securely connected to the flexible surgical instrument housing, and the proximal structural body and the middle connecting body are both located inside the flexible surgical instrument housing; the flexible surgical instrument housing is connected to the multi-motor assembly via the sterile barrier, and the multi-motor assembly comprises a multi-motor assembly housing; and the linear module comprises a support, a fourth motor securely connected to the support, and a linear feed mechanism securely connected to an output shaft of the fourth motor, an output end of the linear feed mechanism is securely connected to the multi-motor assembly housing, and the fourth motor drives the multi-motor assembly by means of the linear feed mechanism, to drive the flexible continuous body structure and the driving unit to perform a linear motion by means of the sterile barrier.

In one embodiment, the linear feed mechanism comprises a screw rod rotatably connected to the support, the screw rod is sheathed with a sliding block which is threadedly fitted with the screw rod, a linear sliding slot is provided on the support, and the sliding block is slidably provided in the linear sliding slot; and the output shaft of the fourth motor is securely connected to the screw rod via a coupling.

The present invention adopts the above technical solutions, and has the following advantages: 1. in the present invention, a flexible continuous body structure comprising a proximal structural body, a middle connecting body and a distal structural body is used as the main body, and is cooperated with a driving unit, wherein the distal structural body is linked to the proximal structural body via the middle connecting body, the driving unit is linked to the proximal structural body, and when the driving unit drives the proximal structural body to be turned in any arbitrary direction, the distal structural body is correspondingly turned in the opposite direction, so as to implement the turning motion in any arbitrary direction of a flexible surgical arm formed of the distal structural body and an envelope; 2. the distal structural body, the middle connecting body and the proximal structural body of the present invention use a redundant structural backbone arrangement (the number of the structural backbones is more than three), which can improve the stability and load capacity of the system; 3. in the present invention, linear motion mechanisms and adapter units are sequentially provided between the driving unit fixing plate and the channel fixing plates, wherein each of the linear motion mechanisms is configured to convert a rotational motion input into a linear motion output, and each of the adapter units is configured to transfer the linear motion of a driving backbone to another driving backbone, and therefore, the cooperative pushing and pulling of the two driving backbones can be realized by inputting a rotational motion to one linear motion mechanism, thereby implementing the freedom of turning of the proximal segment in any arbitrary direction by means of a plurality of linear motion mechanisms; 4. in the present invention, the front end of the distal structural body is provided with a surgical end effector, and a surgical end effector actuation wire passes through the distal structural body and is connected to a surgical end effector driving mechanism in the flexible surgical instrument, such that the surgical end effector driving mechanism can achieve the motion control of the surgical end effector by pushing and pulling the surgical end effector actuation wire; 5. in the present invention, a multi-motor assembly housing is provided, the motor fixing plate and the multi-motor assembly housing are connected in a rotatable manner, an internal ring gear is securely connected to an internal wall of the multi-motor assembly housing, the multi-motor assembly is provided with a motor which is securely connected to the motor fixing plate, an output shaft of the motor is securely connected to an integral rotary input gear which is engaged with the internal ring gear, and the motor can thus drive the rotation of the parts, as a whole, of the system other than the multi-motor assembly housing and the internal ring gear, so that the flexible surgical arm has an overall rotational freedom, thereby achieving adjustment of the roll angle of the surgical end effector; 6. in the present invention, since the flexible surgical instrument housing is connected to the multi-motor assembly via a sterile barrier, thereby effectively isolating sterilized parts, such as the flexible surgical instrument, located in front of the sterile barrier from other unsterilized parts located behind the sterile barrier, and the feasibility of clinical surgery can be thus ensured; and 7. in the present invention, a linear module is further provided, which is partially connected to the multi-motor assembly housing and can drive the flexible surgical instrument, the driving unit and the sterile barrier to a perform linear motion, so that the flexible surgical arm also has a linear feed freedom.

The present invention can be applied to the single-port laparoscopic surgery, and can also be applied to the natural orifice transluminal non-invasive surgery.

DETAILED DESCRIPTION OF EMBODIMENTS

The present invention is described in detail below in conjunction with the accompanying drawings and embodiments.

Figure 1:
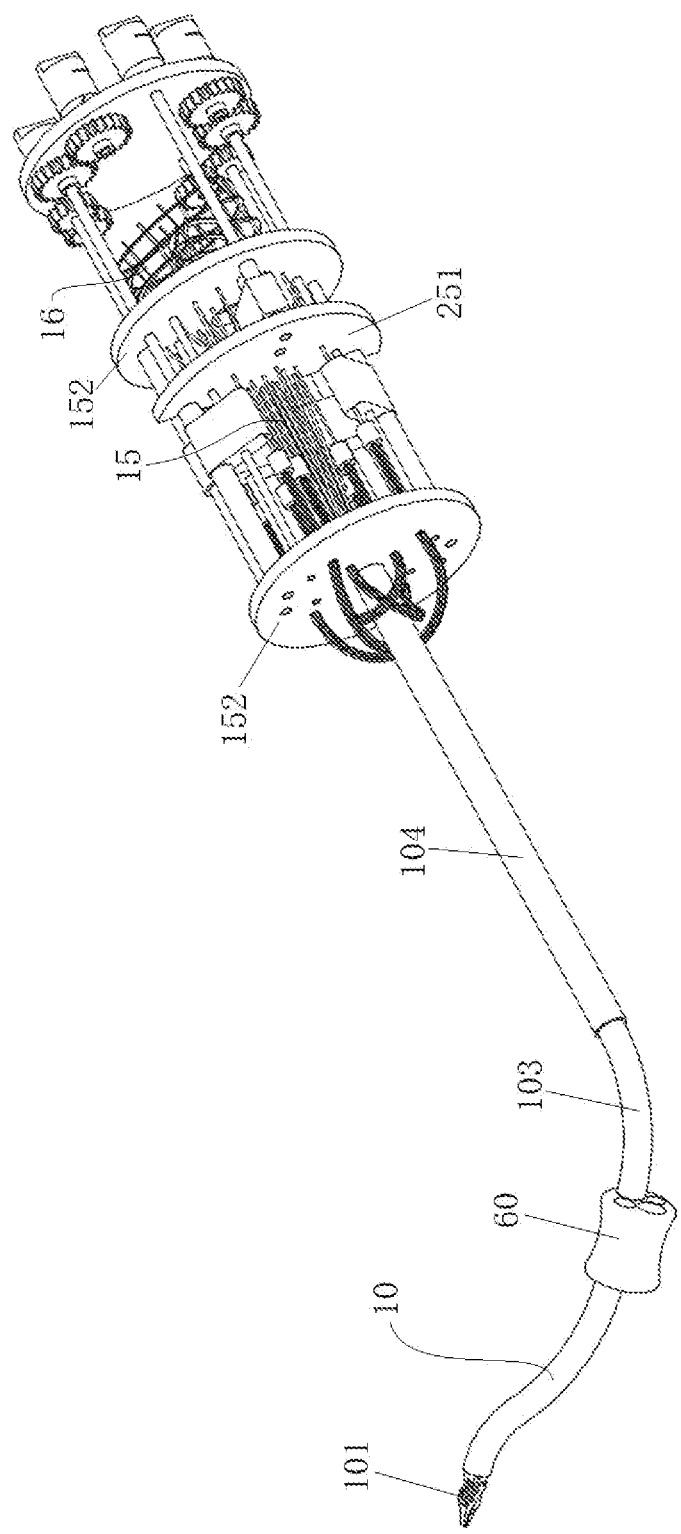
FIG. 1 is an overall structural schematic diagram of the present invention.

As shown in FIG. 1, the present invention comprises a flexible surgical instrument 10 and a driving unit 20.

Figure 2:
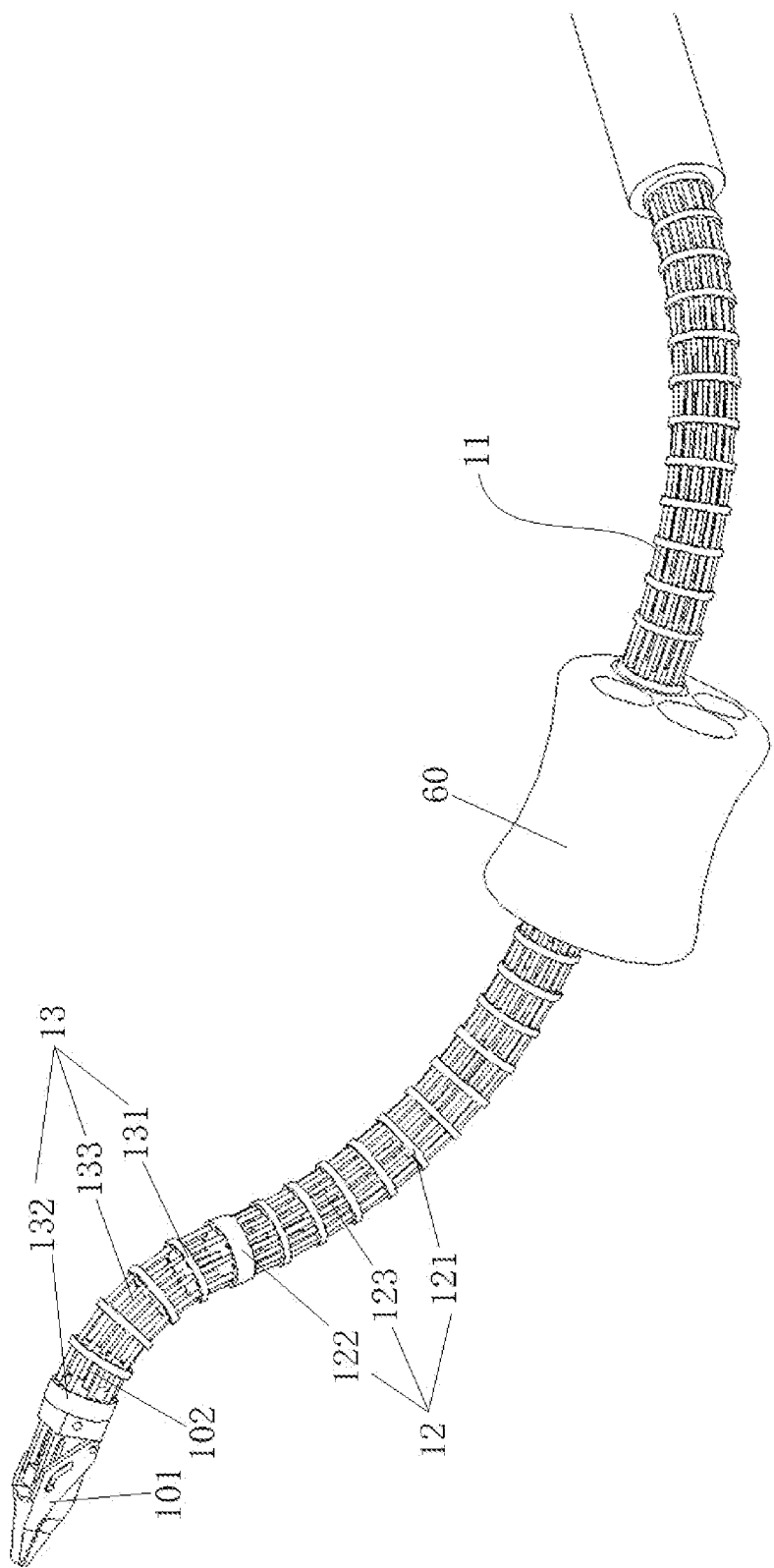
FIG. 2 is a structural schematic diagram of a distal structural body of the present invention.
Figure 3:
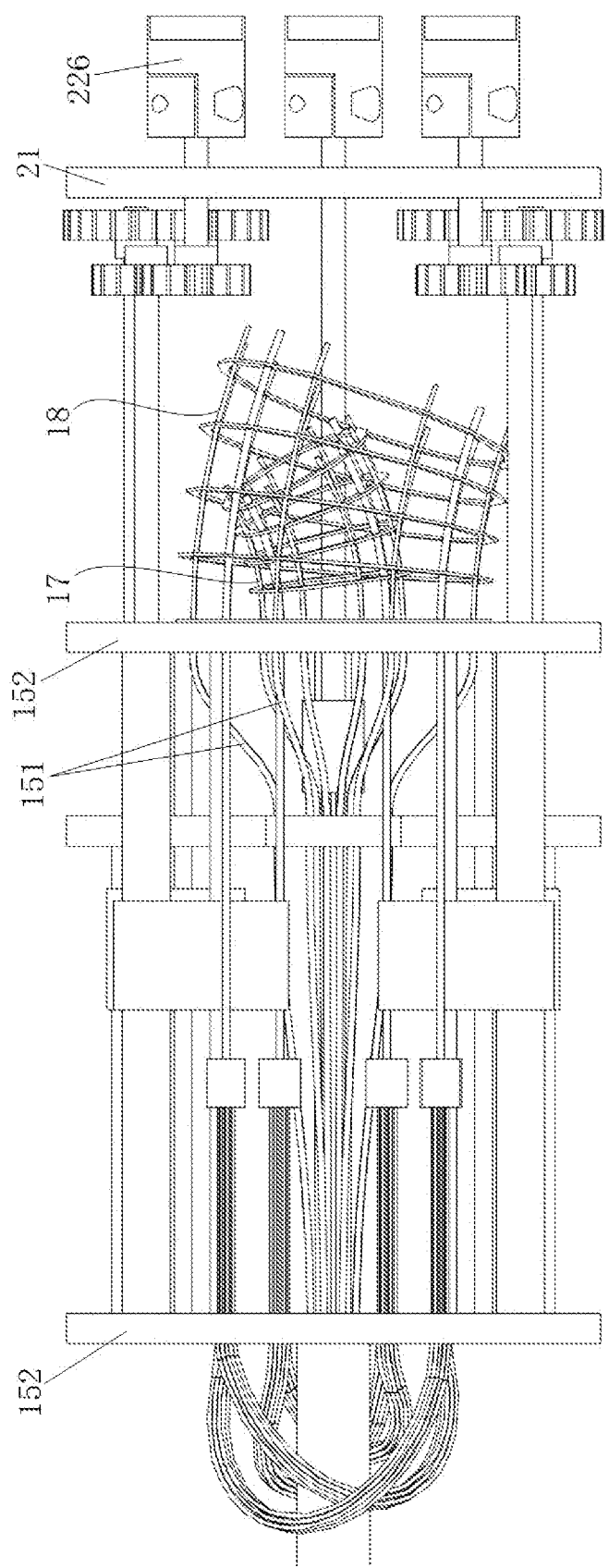
FIG. 3 is a structural schematic view of the present invention with the distal structural body omitted.

As shown in FIGS. 1 to 3, the flexible surgical instrument 10 comprises a flexible continuous body structure composed of a distal structural body 11, a proximal structural body 16 and a middle connecting body 15.

The distal structural body 11 comprises a first distal segment 12 and a second distal segment 13, wherein the first distal segment 12 comprises first distal spacing disks 121, a first distal fixation disk 122 and first segment structural backbones 123. The second distal segment 13 comprises second distal spacing disks 131, a second distal fixation disk 132 and second segment structural backbones 133. The first distal spacing disks 121 and the second distal spacing disks 131 are respectively distributed at intervals in the first distal segment 12 and the second distal segment 13, in order to prevent the first segment structural backbones 123 and the second segment structural backbones 133 from being destabilized when being pushed.

Figure 4:
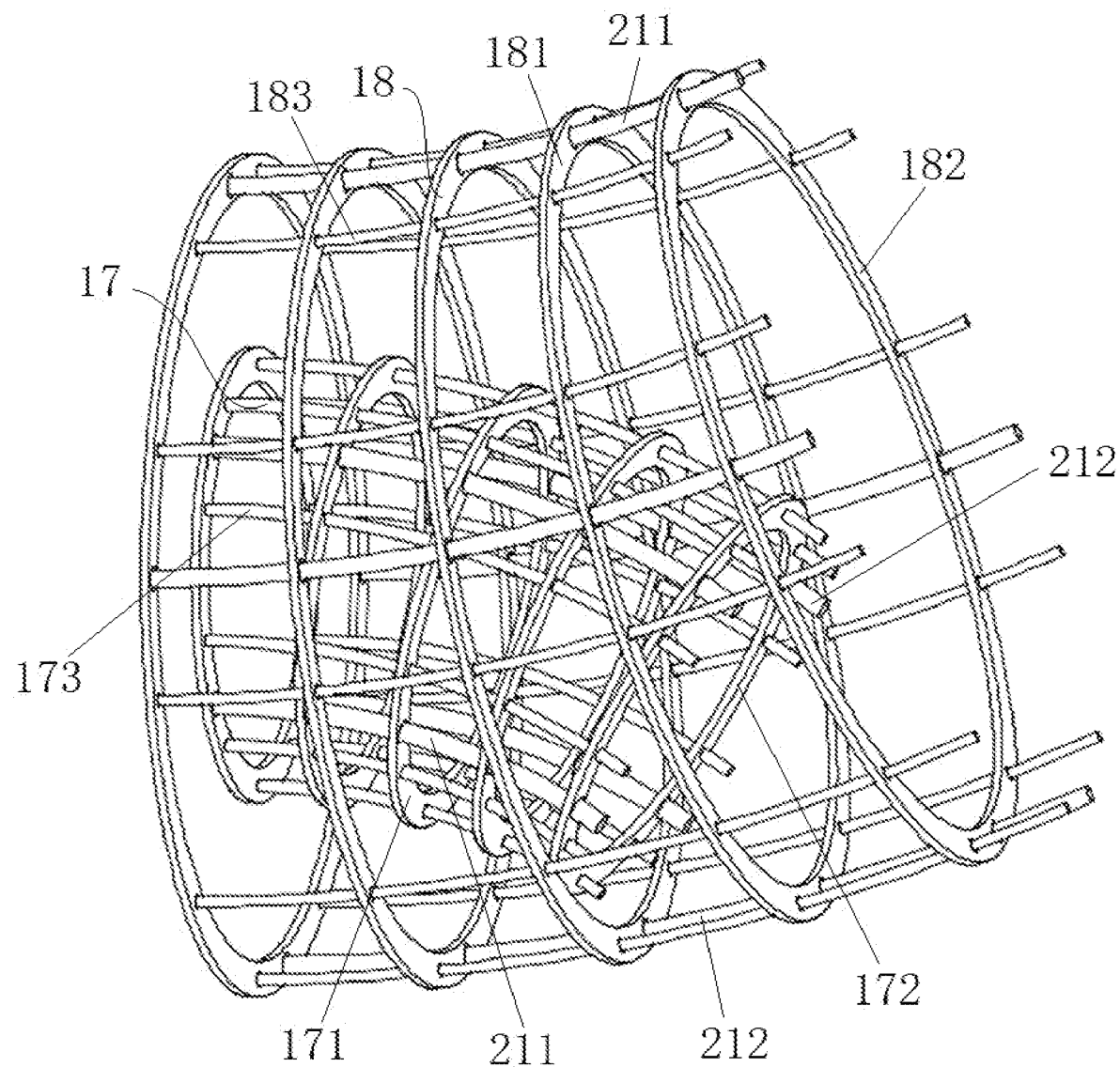
FIG. 4 is a structural schematic diagram of a proximal structural body of the present invention.

The proximal structural body 16 comprises a first proximal segment 17 and a second proximal segment 18, as shown in FIG. 4, wherein the first proximal segment 17 comprises first proximal spacing disks 171, a first proximal fixation disk 172 and first segment structural backbones 173; and the second proximal segment 18 comprises second proximal spacing disks 181, a second proximal fixation disk 182, and second segment structural backbones 183. The first proximal spacing disks 171 and the second proximal spacing disks 181 are respectively distributed at intervals in the first proximal segment 17 and the second proximal segment 18, in order to prevent the first segment structural backbones 173 and the second segment structural backbones 183 from being destabilized when being pushed. The first segment structural backbones 173 of the first proximal segment 17 are securely connected in one-to-one correspondence to or are the same as the first segment structural backbones 123 of the first distal segment 12; and the second segment structural backbones 183 of the second proximal segment 18 are securely connected in one-to-one correspondence to or are the same as the second segment structural backbones 133 of the second distal segment 13. For each of the proximal segments 17, 18 or of the distal segments 12, 13, the number of structural backbones is three or more.

The middle connecting body 15 comprises channel fixing plates 152 and structural backbone guide channels 151 securely connected between the channel fixing plates 152. One end of the first segment structural backbone 173 (123) is securely connected to the first proximal fixation disk 172, and the other end thereof passes through the first proximal spacing disks 171, the structural backbone guide channel 151 and the first distal spacing disks 121 in sequence and is then securely connected to the first distal fixation disk 122. One end of the second segment structural backbone 183 (133) is securely connected to the second proximal fixation disk 182, and the other end thereof passes through the second proximal spacing disks 181, the structural backbone guide channel 151, the first distal segment 12 and the second distal spacing disks 131 and is then securely connected to the second distal fixation disk 132. The structural backbone guide channel 151 functions to keep the shape of the first segment structural backbone 173 (123) and the second segment structural backbone 183 (133) unchanged when being subjected to a pushing or pulling force.

The number of the distal segments comprised in the distal structural body 11 and the number of the proximal segments comprised in the proximal structural body 16 may also be one or more than two, but the number of the proximal segments is always consistent with the number of the distal segments. In addition, when the number of the distal segments is two or more, the distal segments are connected in series, that is, the second distal structural backbone passes through the first distal spacing disks and the first distal fixation disk (and can also pass through the first distal structural backbone if the first distal structural backbone is of a tubular structure). When the number of the proximal segments is two or more, series connection, nested arrangement, independent arrangement, etc. may be used between the segments. In this embodiment, the nested arrangement is used between the two proximal segments (as shown in FIGS. 3 and 4).

Figure 5:
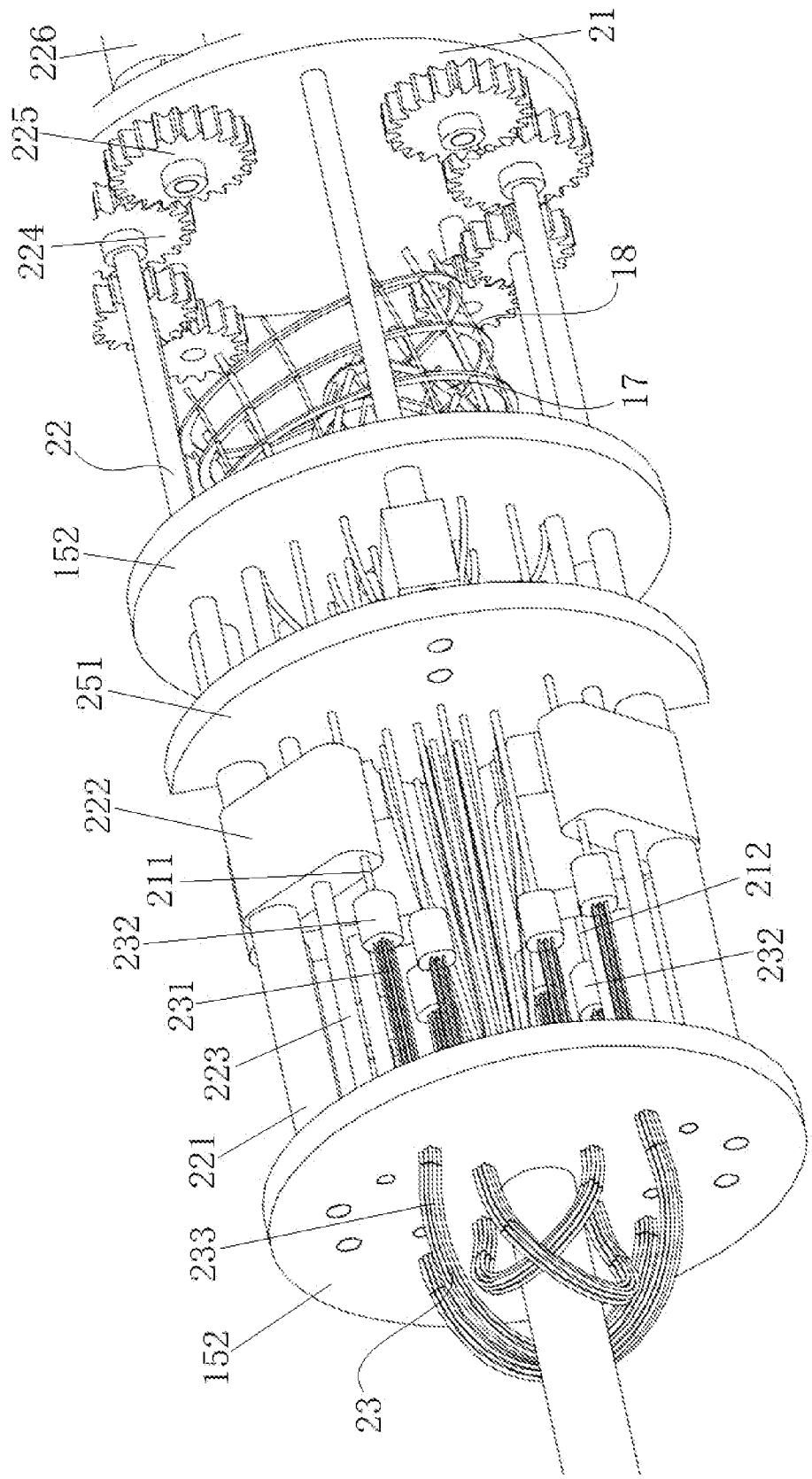
FIG. 5 is a perspective structural schematic diagram of the present invention with the distal structural body omitted.

As shown in FIGS. 3 and 5, the driving unit 20 comprises a driving unit fixing plate 21 provided behind the channel fixing plates 152, and a plurality of linear motion mechanisms 22 are provided between the driving unit fixing plate 21 and the channel fixing plate 152 near the distal structural body 11, and used for converting a rotational motion input into a linear motion output. An output end of each of the linear motion mechanisms 22 is securely connected to a first driving backbone 211, and one end of the first driving backbone 211 is securely connected to one end of a second driving backbone 212 via an adapter unit 23, and the other end of the first driving backbone 211 and the other end of the second driving backbone 212 pass through the first proximal spacing disks 171 and are then securely connected to the first proximal fixation disk 172, or pass through the second proximal spacing disks 181 and are then securely connected to the second proximal fixation disk 182. Two linear motion mechanisms 22 cooperate with the adapter units 23 to push and pull the first driving backbones 211 and the second driving backbones 212 connected to the first proximal segment 17, so that the freedom of turning of the first proximal segment 17 in any arbitrary direction can be achieved, and when the first proximal segment 17 is turned in a certain direction, the first distal segment 12 will be turned in the opposite direction in a certain proportional relationship (determined jointly by the distribution radii of the first segment structural backbone 173 and the first segment structural backbone 123). Similarly, two linear motion mechanisms 22 cooperate with the adapter units 23 to push and pull the first driving backbones 211 and the second driving backbones 212 connected to the second proximal segment 18, so that the freedom of turning of the second proximal segment 18 in any arbitrary direction can be achieved, and when the second proximal segment 18 is turned in a certain direction, the second distal segment 13 will be turned in the opposite direction in a certain proportional relationship (determined jointly by the distribution radii of the second segment structural backbone 183 and the second segment structural backbone 133).

The linear motion mechanism 22 comprises a lead screw 221, a sliding block 222 and a shaft 223, wherein the lead screw 221 is rotatably supported between the two channel fixing plates 152, the rear end of the lead screw 221 passes through the channel fixing plate 152 near the proximal structural body 16 side and extends rearward, the shaft 223 is fixedly connected between the two channel fixing plates 152, and the sliding block 222 is slidably connected to the shaft 223 and is threadly connected to the lead screw 221. The adapter unit 23 comprises a routing backbone 231, structural backbone connectors 232, and a routing backbone guide channel 233, wherein two ends of the routing backbone guide channel 233 are securely connected to a front side of the channel fixing plate 152 near the distal structural body 11 side, the routing backbone 231 passes through the routing backbone guide channel 233, and each of two ends of the routing backbone is respectively securely connected to one structural backbone connector 232, wherein one of the structural backbone connectors 232 is securely connected to the first driving backbone 211, and another structural backbone connector 232 is securely connected to the second driving backbone 212. When the rotational motion is input to the lead screw 221, the rotational motion of the lead screw 221 is converted into the linear motion of the sliding block 222, and the sliding block 222 performing the linear motion directly pushes or pulls the first driving backbone 211 on the one hand, and enables the second driving backbone 212 to perform a push-pull motion opposite to the moving direction of the first driving backbone 211 by means of the structural backbone connectors 232 and the routing backbone 231 on the other hand. Moreover, the turning motion in any arbitrary direction of the first proximal segment 17 or the second proximal segment 18 can be further realized by the cooperative pushing and pulling of the first driving backbone 211 and the second driving backbone 212.

In the above embodiment, the routing backbone 231 may be composed of a plurality of bendable elastic structural backbones which are capable of withstanding a pushing or pulling force, and the distribution of the plurality of elastic structural backbones is preferably in the form of a centrosymmetric distribution with the first driving backbone 211 or the second driving backbone 212 taken as the center. When the distribution of the plurality of elastic structural backbones is not the centrosymmetric distribution with the first driving backbone 211 or the second driving backbone 212 taken as the center, it is necessary to additionally provide a shaft between the two channel fixing plates 152, and the structural backbone connector 232 is slidably connected to the shaft, in order to prevent the structural backbone connector 232 from turning over under the action of the pushing or pulling force.

In the above embodiment, a driven gear 224 is securely connected to the lead screw 221 located on the front side of the driving unit fixing plate 21, the driven gear 224 is engaged with a driving gear 225 rotatably supported on the driving unit fixing plate 21, and a gear shaft of the driving gear 225 passes through the driving unit fixing plate 21 and is securely connected to a male coupling 226. The male coupling 226 is configured to be directly or indirectly connected to a motor in order to input a rotational motion to the lead screw 221.

Figure 6:
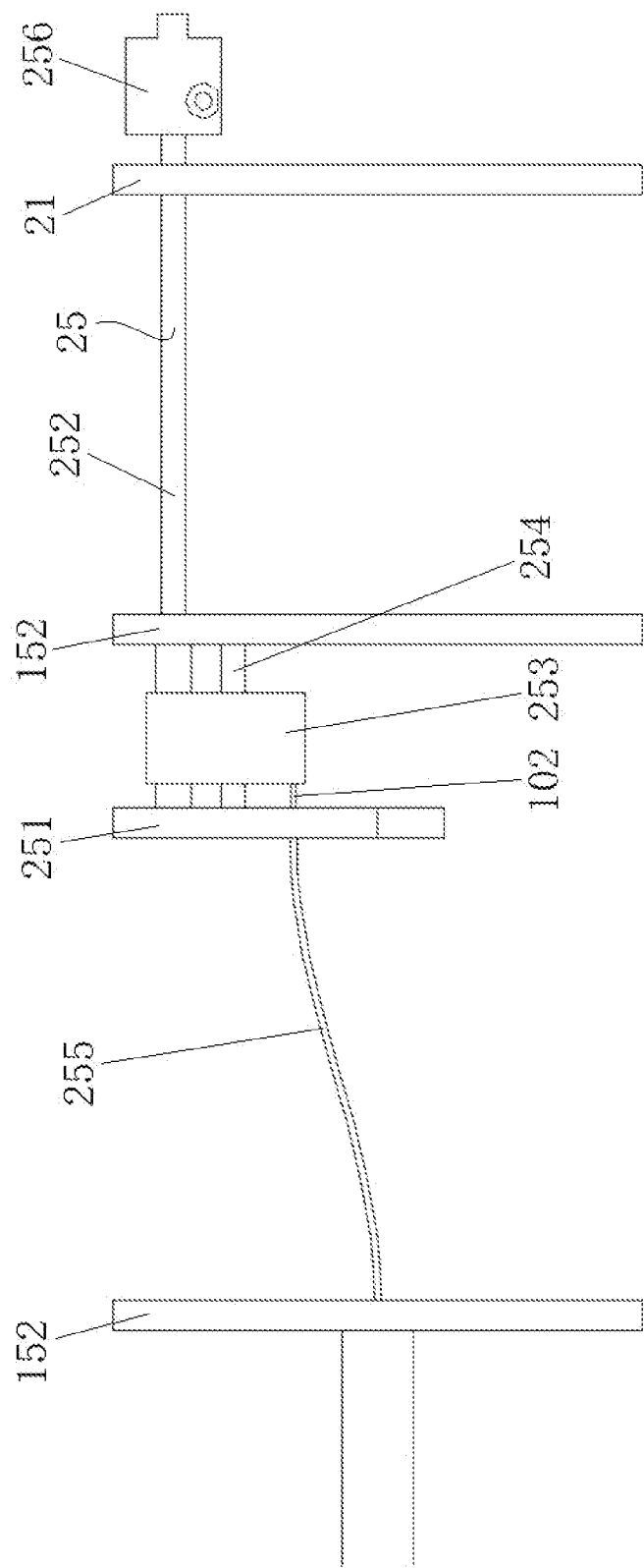
FIG. 6 is a structural schematic diagram of a surgical end effector driving mechanism of the present invention.

In the above embodiment, as shown in FIGS. 1, 5 and 6, a surgical end effector 101 is provided at the front end of the distal structural body 11, and a surgical end effector actuation wire 102 connected at one end to the surgical end effector 101 passes through the distal structural body 11, and is connected at the other end to a surgical end effector driving mechanism 25. The surgical end effector driving mechanism 25 comprises a surgical end effector driving mechanism fixing plate 251 provided between the two channel fixing plates 152, a lead screw 252 is provided between the surgical end effector driving mechanism fixing plate 251 and the driving unit fixing plate 21, the front end of the lead screw 252 passes through the channel fixing plate 152 near the proximal structural body 16 side, a sliding block 253 is connected, by a threaded fit, to the lead screw 252 between the channel fixing plate 152 and the surgical end effector driving mechanism fixing plate 251, the sliding block 253 is slidably provided on a shaft 254, and the shaft 254 is fixedly connected between the channel fixing plate 152 and the surgical end effector driving mechanism fixing plate 251. A actuation wire guide channel 255 is securely connected between the surgical end effector driving mechanism fixing plate 251 and the channel fixing plate 152 near the distal structural body 11 side, and the rear end of the surgical end effector actuation wire 102 passes through the actuation wire guide channel 255 and is then securely connected to the sliding block 253. The actuation wire guide channel 255 functions to keep the shape of the surgical end effector actuation wire 102 unchanged when being subjected to a pushing or pulling force. When a rotational motion is input to the lead screw 252, the rotational motion of the lead screw 252 is converted into a linear motion of the sliding block 253, and the sliding block 253 performing the linear motion can push and pull the surgical end effector actuation wire 102 to implement the motion control of the mechanical surgical end effector 101 (such as a surgical clamp). The rear end of the lead screw 252 passes through the driving unit fixing plate 21 and is securely connected to a male coupling 256, and the male coupling 256 is configured to be directly or indirectly connected to a motor in order to output a rotational motion to the lead screw 252. The surgical end effector actuation wire 102 may also transfer various forms of energy, such as electrical energy and high-frequency vibrations, to achieve specific surgical functions (e.g., electrocoagulation, and electric resection) of the energy-type surgical end effector 101.

In the above embodiment, after the surgical end effector driving mechanism fixing plate 251 is provided between the two channel fixing plates 152, since the distribution radius of the second segment structural backbone 183 is greater than that of the first segment structural backbone 173, the linear motion mechanism 22 linked to the proximal second segment 18 would pass through the surgical end effector driving mechanism fixing plate 251, and the sliding block 222 in the linear motion mechanism 22 slides between the surgical end effector driving mechanism fixing plate 251 and the channel fixing plate 152 near the distal structural body 11 side. Accordingly, the sliding block 222 in the linear motion mechanism 22 linked to the first proximal segment 17 slides between the two channel fixing plates 152.

Figure 7:
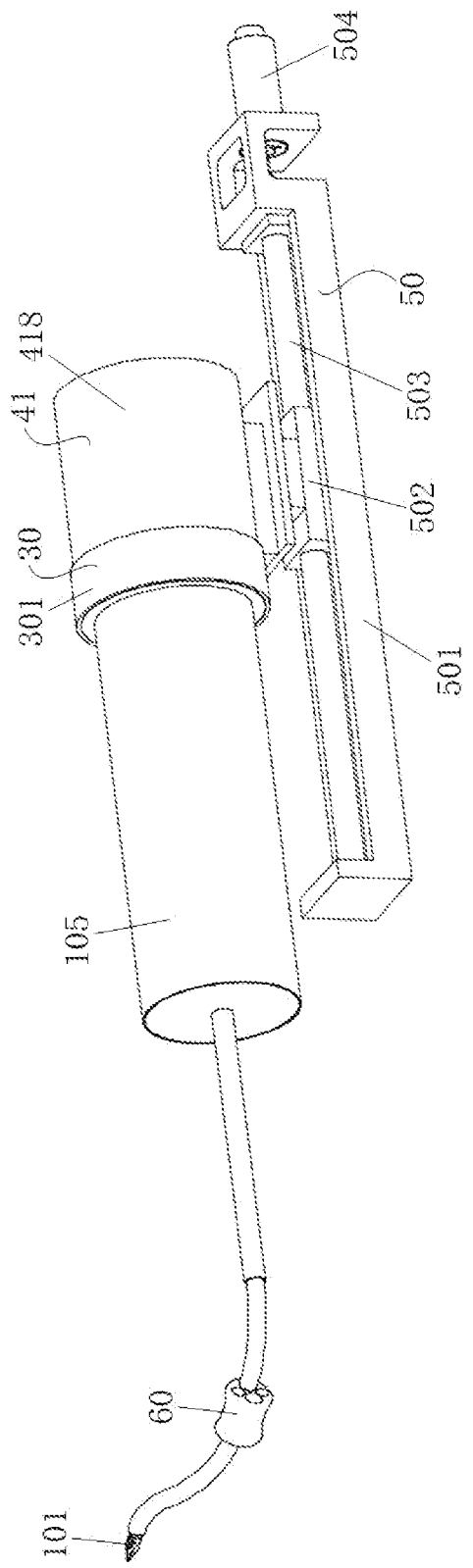
FIG. 7 is a structural schematic view of the present invention with a flexible surgical instrument housing, a multi-motor assembly housing, a sterile barrier and a linear module installed.
Figure 8:
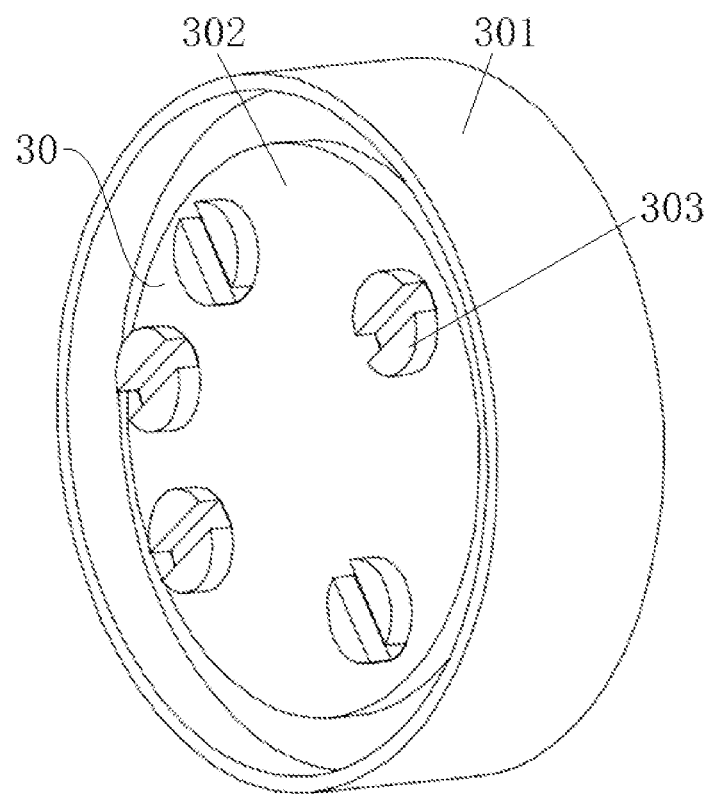
FIG. 8 is a structural schematic diagram of the sterile barrier of the present invention.
Figure 9:
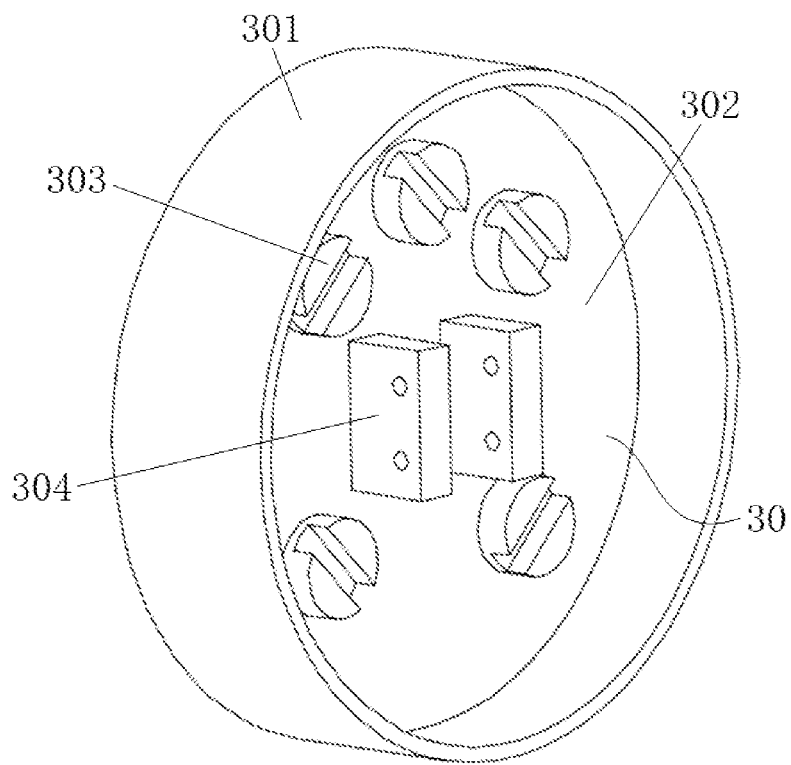
FIG. 9 is a structural schematic view of the sterile barrier of the present invention, but viewed from another angle.
Figure 10:
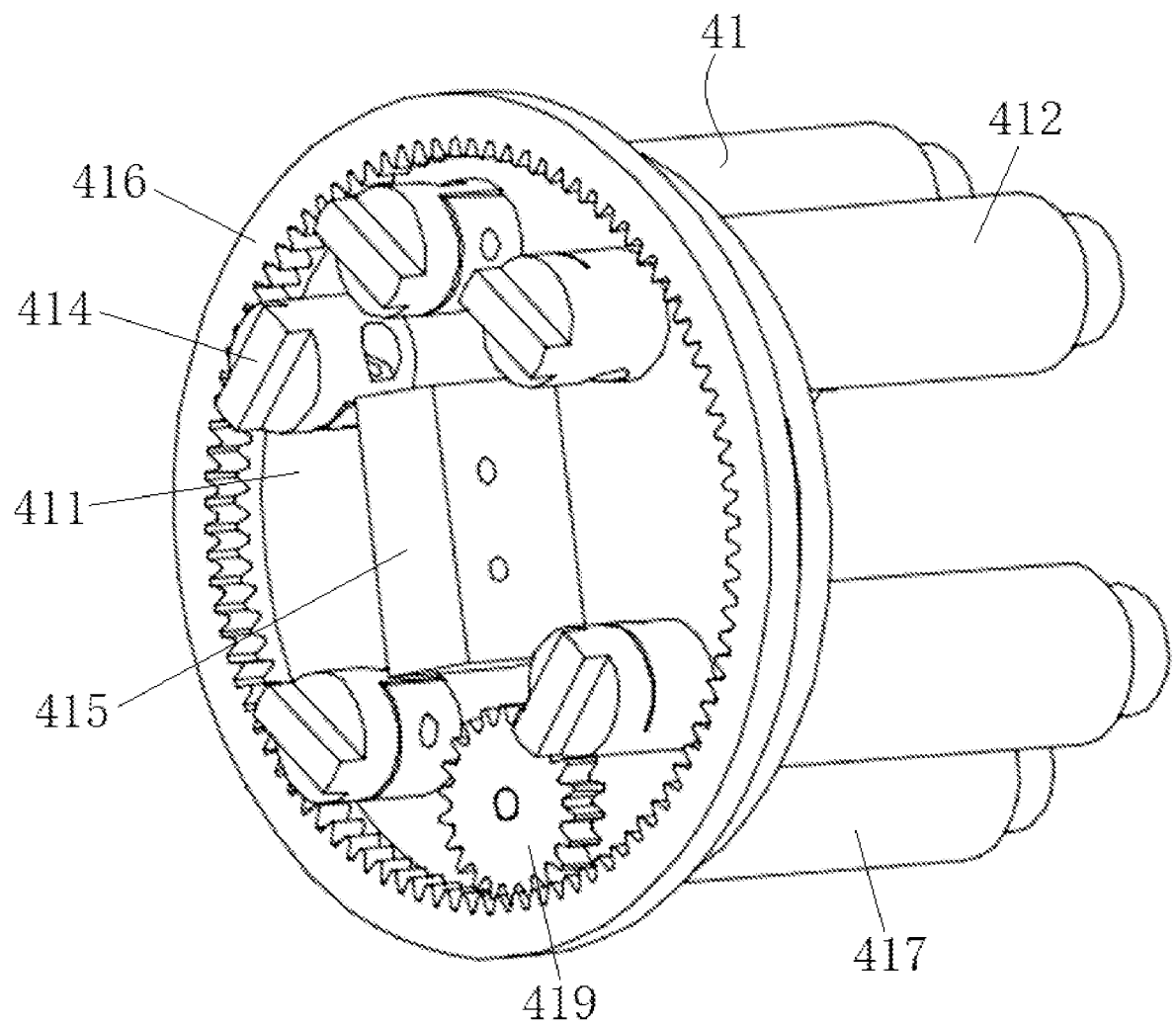
FIG. 10 is a structural schematic diagram of a multi-motor assembly of the present invention.

In the above embodiment, as shown in FIG. 7, the present invention further comprises a flexible surgical instrument housing 105. The driving unit fixing plate 21, the channel fixing plates 152 and the surgical end effector driving mechanism fixing plate 251 are all securely connected to the flexible surgical instrument housing 105; and the proximal structural body 16 and the middle connecting body 15 are both located inside the flexible surgical instrument housing 105. The rear end of the flexible surgical instrument housing 105 is connected to a multi-motor assembly 41 via a sterile barrier 30. As shown in FIGS. 8 and 9, the sterile barrier 30 comprises a sterile barrier support plate 302, a sterile barrier cover 301 securely connected to an outer periphery of the sterile barrier support plate 302, and a plurality of female couplings 303 rotatably connected to the sterile barrier support plate 302. The multi-motor assembly 41 comprises a motor fixing plate 411 (as shown in FIG. 10) and a motor 412 securely connected to the motor fixing plate 411. The front end of the sterile barrier cover 301 and the flexible surgical instrument housing 105 are connected in a quick and detachable manner. Two sets of connecting pin bases 304 are provided on the rear side of the sterile barrier support plate 302. Accordingly, two sets of connecting pin base 415 are provided on the front side of the motor fixing plate 411. The connecting pin bases 304 and the connecting pin bases 415 can be quickly connected via pin holes, such that the sterile barrier 30 is fixedly connected to the motor fixing plate 411 and they can be moved as a whole. The front end of the female coupling 303 is connected to the male coupling 226 or the male coupling 256, and the rear end of the female coupling is connected to an output shaft of the motor 412 via another male coupling 414 to transfer a rotational motion. A sterile membrane (not shown) is securely connected to the sterile barrier cover 301 for isolating unsterilized parts (the parts behind the sterile barrier 30) from sterilized parts (the parts in front of the sterile barrier), to ensure the feasibility of clinical surgery.

In the above embodiment, the present invention further comprises a multi-motor assembly housing 418. The motor fixing plate 411 is rotatably connected to the multi-motor assembly housing 418, an internal ring gear 416 is securely connected to an internal wall of the multi-motor assembly housing 418, and a motor 417 is securely connected to the motor fixing plate 411. An output shaft of the motor 417 is securely connected to an integral rotary input gear 419, and the integral rotary input gear 419 is engaged with the internal ring gear 416. When the output shaft of the motor 417 rotates, the integral rotary input gear 419 is driven to rotate, and the integral rotary input gear 419 travels in a circumferential direction of the internal ring gear 416, thereby driving the rotation of the parts, as a whole, of the present invention other than the multi-motor assembly housing 418 and the internal ring gear 416, and in turn achieving control over the roll angle of the surgical end effector 101.

In the above embodiment, as shown in FIG. 7, the present invention further comprises a linear module 50 (the linear module 50 also being isolated from the sterilized parts via the sterile membrane), which comprises a support 501 with a sliding slot, wherein a screw rod 503 is provided on the support 501, the screw rod 503 is sheathed with a sliding block 502 which is threadedly fitted with the screw rod 503 and slidably provided in the sliding slot, one end of the support 501 is provided with a motor 504, and an output shaft of the motor 504 is securely connected to the screw rod 503 via a coupling. The multi-motor assembly housing 418 is fixedly connected to the sliding block 502. When the output shaft of the motor 504 rotates, the sliding block 502 linearly moves the multi-motor assembly 41, the sterile barrier 30 and the flexible surgical instrument 10 along the sliding slot, thereby achieving the freedom of feeding of the distal structural body 11.

Figure 11:
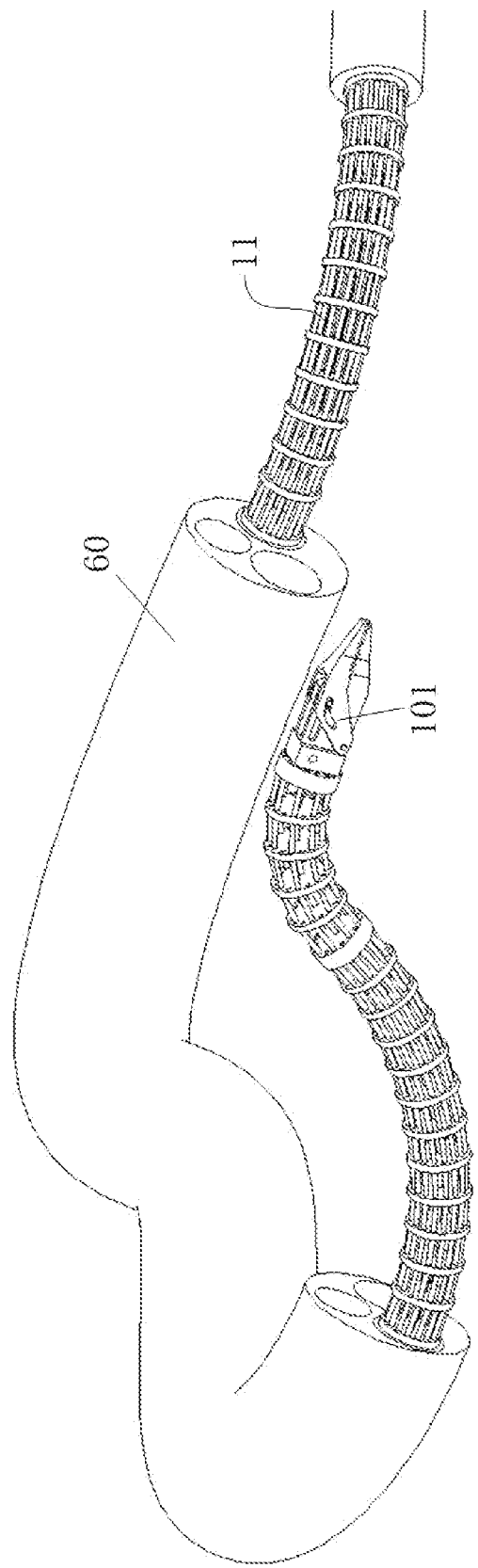
FIG. 11 is a structural schematic diagram of the distal structural body using a flexible sheath of the present invention.

In the above embodiment, as shown in FIGS. 1 and 7, an envelope 103 is provided on the outside of the distal structural body 11 and functions to improve the smoothness of the distal structural body 11 entering a natural orifice or a surgical incision in the human body. A rigid outer sleeve 104 and a sheath 60 may also be provided on the outside of the envelope 103. In an application, the sheath 60 is fixed at a single incision in the abdominal cavity, and the distal structural body 11, together with the envelope 103 and the surgical end effector 101, can freely pass through a through-hole in the sheath 60 for the passage of the surgical instrument and have access to the surgical site to perform the single-port laparoscopic surgery. As shown in FIG. 11, the sheath 60 may also be a flexible sheath that can more easily extend into various natural orifices of the human body and adaptively change shape as the shape of the orifices, one end of the flexible sheath is fixed at the entrance of the orifice, and the distal structural body 11, together with the envelope 103 and the surgical end effector 101, can freely pass through a through-hole in the flexible sheath for the passage of the surgical instrument and have access to the surgical site to perform non-invasive surgery through the natural orifice.

The present invention has been illustrated only by the above embodiments, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument, comprising:
a distal structural body comprising at least one distal structural segment, the at least one distal structural segment comprising a distal fixation disk and structural backbones;
a proximal structural body comprising at least one proximal structural segment, the at least one proximal structural segment comprising a proximal fixation disk, structural backbones, a first driving backbone, and a second driving backbone, the structural backbones of the distal structural segment being securely connected in one-to-one correspondence to or the same as corresponding structural backbones of the proximal structural segment;
a linear motion mechanism operable to convert a rotational motion into a linear motion of an output end of the linear motion mechanism; and
an adapter unit comprising:
a routing backbone comprising two ends securely connected to a first driving structure backbone and a second driving structure backbone, respectively,
wherein the output end of the linear motion mechanism is securely connected to the first driving structure backbone and operable to cooperatively push-pull the first driving backbone and the second driving backbone to turn the proximal structural segment.

2. The flexible surgical instrument of claim 1, wherein the adapter unit comprises a routing backbone guide channel, the routing backbone passing through the routing backbone guide channel.

3. The flexible surgical instrument of claim 1, wherein:
proximal ends of the structural backbones of the proximal structural segment are securely connected to the proximal fixation disk; and
distal ends of the structural backbones of the distal structural segment are securely connected to the distal fixation disk.

4. The flexible surgical instrument of claim 1, wherein a first end of the first driving structure backbone and a first end of the second driving structure backbone are securely connected to the proximal fixation disk.

5. The flexible surgical instrument of claim 1, wherein:
the proximal structural segment further comprises proximal spacing disks, the structural backbones of the proximal structural segment passing through the proximal spacing disks; and
the distal structural segment further comprises distal spacing disks, the structural backbones of the distal structural segment passing through the distal spacing disks.

6. The flexible surgical instrument of claim 1, wherein the adapter unit further comprises:
a first structure backbone connector disposed in a first end of the routing backbone and securely connected to a second end of the first driving structure backbone; and
a second structure backbone connector disposed in a second end of the routing backbone and securely connected to a second end of the second driving structure backbone.

7. The flexible surgical instrument of claim 1, wherein the routing backbone comprises a plurality of elastic structural backbones.

8. The flexible surgical instrument of claim 1, wherein the linear motion mechanism comprises:
a first lead screw to receive the rotational motion; and
a first sliding block in a threaded connection with the first lead screw and securely connected to the first driving structure backbone.

9. The flexible surgical instrument of claim 1, further comprising:
a surgical end effector disposed at a distal end of the distal structural body; and
a surgical end effector actuation wire passing through the distal structural body, the surgical end effector actuation wire comprising a proximal end securely connected to a surgical end effector driving mechanism and a distal end securely connected to the surgical end effector.

10. The flexible surgical instrument of claim 2, further comprising a middle connecting body, the middle connecting body comprising:
a first channel fixing plate close to the distal structural body;
a second channel fixing plate close to the proximal structural body; and
structural backbone guide channels disposed between the first channel fixing plate and the second channel fixing plate, wherein:
the structural backbones of the distal structural segment pass through the structural backbone guide channels; and
distal ends of the structural backbones of the distal structural segment are securely connected to the distal fixation disk.

11. The flexible surgical instrument of claim 8, further comprising:
a driven gear securely connected to a proximal end of the first lead screw; and
a driving gear engaged with the driven gear.

12. The flexible surgical instrument of claim 9, wherein the surgical end effector driving mechanism comprises:
a second lead screw; and
a second sliding block in a threaded connection with the second lead screw and connected to the proximal end of the surgical end effector actuation wire.

13. The flexible surgical instrument of claim 10, wherein two ends of the routing backbone guide channel are securely connected to a front side of the first channel fixing plate.

14. The flexible surgical instrument of claim 12, wherein the surgical end effector driving mechanism further comprises:
an actuation wire guide channel, the surgical end effector actuation wire passing through the actuation wire guide channel.

15. A flexible surgical instrument system, comprising:
a flexible surgical instrument comprising:
a distal structural body comprising at least one distal structural segment, the at least one distal structural segment comprising a distal fixation disk and structural backbones;
a proximal structural body comprising at least one proximal structural segment, the at least one proximal structural segment comprising a proximal fixation disk, structural backbones, a first driving backbone, and a second driving backbone, the structural backbones of the distal structural segment being securely connected in one-to-one correspondence to or the same as corresponding structural backbones of the proximal structural segment;
a linear motion mechanism operable to convert a rotational motion into a linear motion of an output end of the linear motion mechanism; and
an adapter unit comprising:
a routing backbone comprising two ends securely connected to a first driving structure backbone and a second driving structure backbone, respectively, wherein the output end of the linear motion mechanism is securely connected to the first driving structure backbone and operable to cooperatively push-pull a first driving backbone and a second driving backbone to turn the proximal structural segment; and
a driving unit configured to input the rotational motion to the linear motion mechanism.

16. The flexible surgical instrument system of claim 15, further comprising:
a linear module configured to drive the flexible surgical instrument and the driving unit to perform another linear motion.

17. The flexible surgical instrument system of claim 15, further comprising:
a flexible surgical instrument housing, the proximal structural body being disposed in the flexible surgical instrument housing;
a motor assembly; and
a sterile barrier disposed between the flexible surgical instrument housing and the motor assembly.

18. The flexible surgical instrument system of claim 17, wherein:
the motor assembly comprises:
a motor fixing plate; and
a motor securely connected to the motor fixing plate; and
the linear motion mechanism comprises:
a first lead screw connected to the motor; and
a first sliding block in a threaded connection with the first lead screw and securely connected to the first driving structure backbone.

19. The flexible surgical instrument system of claim 17, wherein the sterile barrier comprises:
a sterile barrier support plate; and
a sterile barrier cover securely connected to an outer periphery of the sterile barrier support plate.

20. The flexible surgical instrument system of claim 19, wherein the motor assembly comprises:
a motor fixing plate connected to the sterile barrier support plate;
a motor assembly housing, the motor fixing plate being rotatably connected to the motor assembly housing;
an internal ring gear securely connected to an internal wall of the motor assembly housing; and
an input gear engaged with the internal ring gear, the input gear being securely connected to a shaft.

\* \* \* \* \*